United States Patent [19]

Felix

[11] Patent Number: 4,487,724

[45] Date of Patent: Dec. 11, 1984

[54] METHOD FOR PREPARATION OF N-PHOSPHONOMETHYLGLYCINE

[75] Inventor: Raymond A. Felix, Richmond, Calif.

[73] Assignee: Stauffer Chemical Company, Westport, Conn.

[21] Appl. No.: 553,451

[22] Filed: Nov. 21, 1983

Related U.S. Application Data

[62] Division of Ser. No. 410,802, Aug. 23, 1982, Pat. No. 4,429,124.

[51] Int. Cl.$^3$ ............................................. C07F 9/38
[52] U.S. Cl. ........................... 260/502.5 F; 260/940; 260/941
[58] Field of Search ..................... 260/502.5 F

[56] References Cited

U.S. PATENT DOCUMENTS

| | | | |
|---|---|---|---|
| 3,923,877 | 12/1975 | Barton | 260/502.5 F |
| 4,053,505 | 10/1977 | Dutra | 260/502.5 F |
| 4,425,283 | 1/1984 | Felix | 260/502.5 F |
| 4,425,284 | 1/1984 | Felix | 260/502.5 F |
| 4,427,599 | 1/1984 | Felix | 260/502.5 F |
| 4,444,693 | 4/1984 | Felix | 260/502.5 F |

Primary Examiner—J. E. Evans
Attorney, Agent, or Firm—Edwin H. Baker

[57] ABSTRACT

A method for preparing N-phosphonomethylglycine comprising (a) O,O-dialkylaminomethylphosphonate with formaldehyde to produce a triazine; (b) reacting the triazine formed in step (a) with an acyl halide to form the O,O-dialkyl-N-phosphonomethyl-N-chloromethyl acetamide of the acyl halide; (c) reacting the amide formed in step (b) with metal cyanide to form O,O-dialkyl-N-cyanomethyl-N-acetamide; and (d) hydrolyzing the acetamide formed in step (c) to yield N-phosphonomethylglycine.

9 Claims, No Drawings

METHOD FOR PREPARATION OF N-PHOSPHONOMETHYLGLYCINE

This is a divisional of application Ser. No. 410,802, filed Aug. 23, 1982, now U.S. Pat. No. 4,429,124.

FIELD OF THE INVENTION

This invention is a new process for preparing N-phosphonomethylglycine.

BACKGROUND OF THE INVENTION

N-Phosphonomethylglycine and certain salts are particularly effective as post-emergence herbicides. The commercial herbicide is sold as a formulation containing the isopropylamine salt of N-phosphonomethylglycine.

N-Phosphonomethylglycine can be made by a number of methods. One such method, as described in U.S. Pat. No. 3,160,632 is to react N-phosphinomethylglycine (glycinemethylenephosphonic acid) with mercuric chloride in water at reflux temperature, and subsequently separating the reaction products. Other methods are phosphonomethylation of glycine and the reaction of ethyl glycinate with formaldehyde and diethylphosphite. The latter method is described in U.S. Pat. No. 3,799,758. In addition, there is a series of patents relating to the preparation of N-phosphonomethylglycine, including U.S. Pat. Nos. 3,868,407, 4,197,254 and 4,199,354.

Close prior art is U.S. Pat. No. 3,923,877, which teaches the reaction of 1,3,5-tricyanomethylhexahydro-1,3,5-triazine with excess disubstituted phosphite to form $(RO)_2P(O)CH_2NHCH_2CN$ (R is hydrocarbyl or substituted hydrocarbyl) which is hydrolyzed to yield N-phosphonomethylglycine.

Because of the commercial importance of N-phosphonomethylglycine and certain salts as herbicides, improved methods of preparing these compounds are valuable.

BRIEF DESCRIPTION OF THE INVENTION

This invention relates to a process for preparing N-phosphonomethylglycine which comprises:

(1) reacting O,O-dialkylaminomethylphosphonate with formaldehyde to produce N,N',N''-tris[O,O-dialkylphosphonomethyl]hexahydro-1,3,5-triazine;

(2) reacting the triazine with an acyl halide, preferably acyl chloride, to form th O,O-dialkyl-N-phosphonomethyl-N-chloromethyl acetamide of the acyl halide;

(3) reacting the amide with a metal cyanide to form O,O-dialkyl-N-phosphonomethyl-N-cyanomethyl-N-acetamide; and (4) hydrolyzing this acetamide to yield N-phosphonomethylglycine.

Detailed Description of the Invention

The process of this invention may be illustrated by the following reaction scheme:

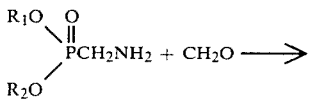 (a)

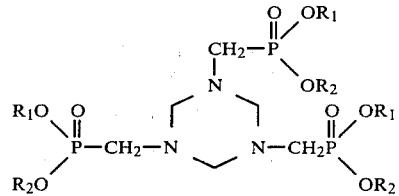

wherein $R_1$ and $R_2$ are both aromatic or aliphatic groups as defined hereinafter, preferably $R_1$ and $R_2$ and $C_1$–$C_6$ alkyl, more preferably $C_1$–$C_4$ alkyl, most preferably ethyl.

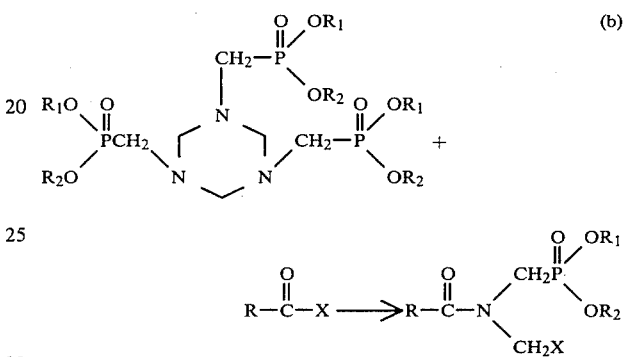

wherein R is an aliphatic or aromatic group as defined hereinafter, preferably $C_1$–$C_4$ alkyl, most preferably methyl or ethyl, X is chlorine, bromine, or iodine, most preferably chlorine, and $R_1$ and $R_2$ are defined as above.

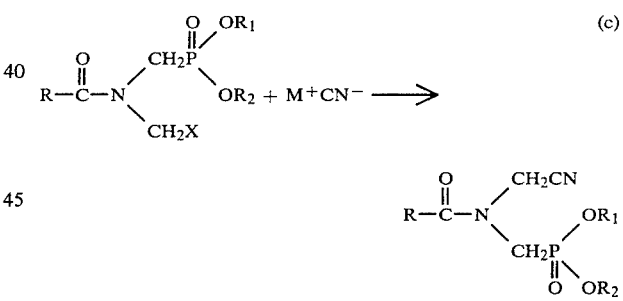

wherein R, X, $R_1$ and $R_2$ are defined as above and M is a metal, preferably an alkali metal, most preferably potassium,

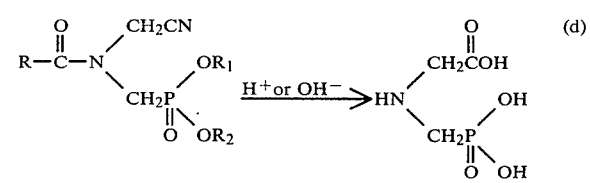

wherein R, $R_1$ and $R_2$ are as defined above and $H^+$ is a strong acid such as hydrochloric, hydrobromic, hydriodic, nitric, sulfuric, phosphonic or chloroacetic acid. Preferably $H^+$ is hydrochloric or hydrobromic acid and $OH^-$ is a strong base such as sodium hydroxide or potassium hydroxide, preferably in an aqueous, aqueous-alcoholic or alcoholic solution. Preferably, the hydrolysis is run in the presence of a strong acid.

In the above reaction scheme, the groups $R_1$ and $R_2$ are not directly involved in reaction step (a) between O,O-dialkylaminomethylphosphonate and formaldehyde.

Groups R, $R_1$ and $R_2$ are not directly involved in reaction step (b) between N,N',N''-tris[O,O-dialkylphosphonomethyl]hexahydrotriazine and the acyl halide. Groups R, $R^1$ or $R^2$ are not directly involved in reaction step (c) between the O,O-dialkyl-N-phosphonomethyl-N-chloromethyl acetamide reaction product of step (b) and the potassium cyanide. Groups R, $R^1$ and $R^2$ are removed in reaction step (d) when the acetamide reaction product of reaction step (c) is subjected to hydrolysis. Therefore, the nature of groups R, $R^1$ and $R^2$ is not critical, although groups which would interfere with reaction steps (b) and (c) are to be avoided.

The group "$C_1$-$C_4$ alkyl" encompasses methyl, ethyl, n-propyl, isopropyl, n-butyl, isobutyl, sec-butyl, and tert-butyl. The group "$C_1$-$C_6$ alkyl" encompasses the same radicals as $C_1$-$C_4$ alkyl plus the 6 pentyls and the 16 hexyls.

The term "aliphatic group" is used in a broad sense to cover a large class of organic groups characterized by being derived from (1) an acylic (open-chain structure) of the paraffin, olefin and acetylene hydrocarbon series and their derivatives or (2) alicyclic compounds. The aliphatic group can have from 1 to 10 carbon atoms.

The term "aromatic group" is used in a broad sense to distinguish from the aliphatic group and includes a group derived from (1) compounds having 6 to 20 carbon atoms and characterized by the presence of at least one benzene ring, including monocyclic, bicyclic and polycyclic hydrocarbons and their derivatives and (2) heterocyclic compounds having 5 to 19 carbon atoms which are similar in structure and are characterized by having an unsaturated ring structure containing at least one atom other than carbon such as nitrogen, sulfur and oxygen and derivatives of these heterocyclic compounds.

Reaction step (a) preferably is run at a temperature between about 0° to about 100° C., more preferably between about 0° to about 45° C. and most preferably between about 0° to about 20° C. This reaction step can be run at atmospheric, sub-atmospheric or super-atmospheric pressure, preferably at atmospheric pressure. Preferably the reaction is run in a solvent for the amine, such as ethylene dichloride, methylene chloride, or toluene. One mole of formaldehyde is needed to react with one mole of O,O-diethylaminomethylphosphonate. An excess of formaldehyde can be used to insure complete reaction with the phosphonate.

Reaction step (b) is preferably run at a temperature between about −20° to about 110° C., more preferably between about 20° to about 80° C. This reaction step can be run at atmospheric, sub-atmospheric, or superatmospheric pressure, preferably at atmospheric pressure. Preferably the reaction is run in a solvent for the phosphonate, such as dichloromethane, dichloroethane, toluene, or ethyl acetate.

Three moles of the acyl halide are needed to react with one mole of the N,N',N''-tris(O,Odialkylphosphonomethyl)hexahydrotriazine; furthermore, an excess of the acyl halide can be used to insure complete reaction with the triazine. The solvent or any excess acyl halide can be removed to isolate the O,O-dialkyl-N-phosphonomethyl-N-chloromethyl acetamide of the acyl halide in high yields. However, this amide quickly degrades by hydrolysis and should be kept in an inert atmosphere.

In reaction step (c), most preferably a mole amount of the O,O-diethyl-N-phosphonomethyl-N-chloromethyl acetamide and excess potassium cyanide are reacted. Less preferably, a large mole excess can be used. The reaction can be run at a temperature between about 0° C. to about 100° C., more preferably between about 20° C. to about 30° C. Preferably the reaction is run in a solvent, such as acetonitrile, dioxane, dimethylformamide, or dimethylsulfoxide.

In reaction step (d), a mole of the phosphonate reaction product from reaction step (c) is hydrolzed with 5 moles of water. The hydrolysis is run in the presence of a strong acid or base as defined above. Preferably the hydrolysis is acid-catalyzed, preferably with an inorganic acid, and most preferably with hydrochloric or hycrobromic acid. The hydrolysis yields the desired N-phosphonomethylglycine. Preferably at least 2 moles of the acid are used. More preferably, a large excess over the 2 mole amount is used. The preferred hydrochloric or hydrobromic acid can be used in concentrated or aqueous form.

This last reaction step is run at a temperature between about 0° to about 200° C., preferably between 50° to about 125° C. and most preferably between about 100° to about 125° C.

Atmospheric, sub-atmospheric or super-atmospheric pressure can be used. Preferably atmospheric pressure is used during the hydrolysis.

The solid N-phosphonomethylglycine can be recovered by conventional techniques in reaction step (c). Volatile liquid products such as alcohols (methanol) chlorides (methyl chloride), acids (acetic acid), water, and excess acid can be removed by standard stripping techniques. The desired N-phosphonomethylglycine is removed in high purity by dissolving it in water, adjusting the pH of the solution to between 1 and 2, allowing it to crystallize from solution and removing it by filtration.

The process of this invention can be better understood by reference to the following specific examples.

EXAMPLE I

Preparation of N,N',N''-Tris[O,O-diethylphosphonomethyl]hexahydro-s-triazine

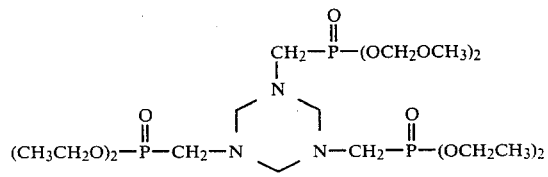

In a 50 milliliter (ml) flask, 5.1 grams (g) (0.03 mole) of O,O-diethylaminomethylphosphonate was dissolved with stirring in 15 ml of dichloromethane and cooled to 5° C. in an ice bath. Next, 3.0 g (0.03 mole) of 37% formaldehyde in 10 ml of water was added, and the mixture was stirred one hour at room temperature. Ten ml of water was added, then the aqueous layer was extracted three times with 25 ml of dichloromethane. After drying with magnesium sulfate, the solvent was evaporated to yield 5.2 g of the desired product. The structure was confirmed by proton nuclear magnetic resonance and infrared.

EXAMPLE II

Preparation of O,O-diethyl-N-phosphonomethyl-N-chloromethyl acetamide

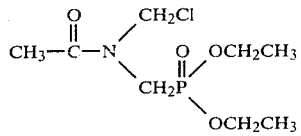

Four and four tenths grams (0.0082 mole) of N,N',N''-tris[O,O-diethylphosphonomethyl]hexahydrotriazine was dissolved with stirring in 20 ml of ethylene dichloride in a 50 ml flask. Two ml (0.028 mole) of acetyl chloride was then added all at once, resulting in an exothermic reaction. The solution was stirred at room temperature overnight, then stripped under reduced pressure to yield 6.3 g of O,O-diethyl-N-phosphonomethyl-N-chloromethyl acetamide. The structure was confirmed by proton nuclear magnetic resonance.

EXAMPLE III

Preparation of O,O-diethyl-N-phosphonomethyl-N-cyanomethyl-N-acetamide

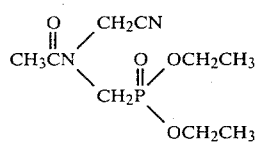

The amide compound prepared in Example II (6.3 g, 0.025 mole), 2.0 g (0.031 mole) of powdered potassium cyanide, 0.1 g of 18-crown-6 (1,4,7,10,13,16-hexaoxacyclooctadecane), and 5 ml of acetonitrile were combined in a 50 ml flask and stirred approximately 72 hours at ambient temperature. Next, 20 ml of water was added and the solution was stirred one-half hour. The solution was then extracted twice with 100 ml of dichloromethane. The organic layers were combined, dried and stripped under reduced pressure to yield 4.8 g of the desired product. The structure was confirmed by usual analytical methods (proton nuclear magnetic resonance, $^{13}C$ nuclear magnetic resonance, mass spectroscopy, and infrared.

EXAMPLE IV

Preparation of N-phosphonomethylglycine

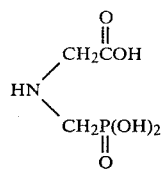

The acetamide reaction product from Example III (4.8 g, of 0.0194 mole) was combined with 50 ml of concentrated hydrochloric acid in a 100 ml flask and refluxed three hours. The solution was stripped under reduced pressure to yield 3.9 g of N-phosphonomethylglycine. The structure was confirmed by proton nuclear magnetic resonance, $^{13}C$ nuclear magnetic resonance, and liquid chromatography techniques.

What is claimed is:

1. A method of preparing N-phosphonomethylglycine comprising
   (a) reacting O,O-dialkylaminomethylphosphonate with formaldehyde to produce a triazine compound of the formula

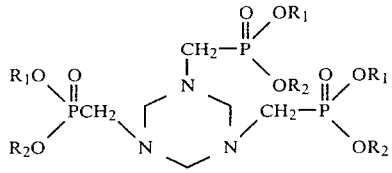

wherein $R_1$ and $R_2$ are both aromatic or aliphatic groups;
   (b) reacting the triazine formed in step (a) with an acyl halide of the formula

wherein X is chlorine, bromine, or iodine and R is an aliphatic or aromatic group to form the O,O-dialkyl-N-phosphonomethyl-N-chloromethyl acetamide of the acyl halide, which has the formula

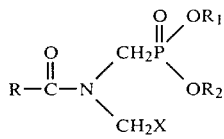

wherein R, $R_1$, $R_2$ and X are as defined,
   (c) reacting the amide formed in step (b) with metal cyanide to form O,O-dialkyl-N-cyanomethyl-Nacetamide, which has the structural formula

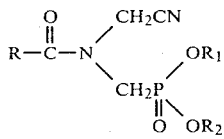

wherein R, $R_1$ and $R_2$ are as defined; and
   (d) hydrolyzing the acetamide formed in step (c) to yield N-phosphonomethylglycine.

2. The method of claim 1 wherein R is $C_1$–$C_4$ alkyl and X is chlorine.

3. The method of claim 1 wherein R is $C_1$–$C_4$ alkyl, $R_1$ is $C_1$–$C_6$ alkyl, $R_2$ is $C_1$–$C_6$ alkyl and X is chlorine.

4. The method of claim 1 wherein R is $C_1$–$C_2$ alkyl, $R_1$ is $C_1$–$C_4$ alkyl, $R_2$ is $C_1$–$C_4$ alkyl and X is chlorine.

5. The method of claim 1 wherein R is $C_1$–$C_2$ alkyl, $R_1$ is $C_1$–$C_2$ alkyl, $R_2$ is $C_1$–$C_2$ alkyl, and X is chlorine.

6. The method of claim 1 wherein R is methyl, $R_1$ is ethyl and $R_2$ is ethyl.

7. The method of claim 1 wherein step (b) is run at a temperature between about 0° C. to about 150° C.

8. The method of claim 7 wherein an acid catalyst is used in step (d).

9. The method of claim 8 wherein the acid catalyst is hydrochloric or hydrobromic acid.

* * * * *